United States Patent [19]

Rembaum et al.

[11] 4,267,235
[45] May 12, 1981

[54] POLYGLUTARALDEHYDE MICROSPHERES

[75] Inventors: Alan Rembaum, Altadena; Shlomo Margel, N. Hollywood, both of Calif.

[73] Assignee: California Institute of Technology, Pasadena, Calif.

[21] Appl. No.: 21,988

[22] Filed: Mar. 19, 1979

[51] Int. Cl.$^3$ ............................................. B32B 5/16
[52] U.S. Cl. ..................................... 428/407; 252/67; 260/112 R; 528/245; 528/246; 528/263; 528/270; 428/406
[58] Field of Search ............... 428/407, 406, 332, 403; 528/245, 270, 263, 246; 260/112 R; 252/67

[56] References Cited

U.S. PATENT DOCUMENTS

| | | | |
|---|---|---|---|
| 3,957,741 | 5/1976 | Rembaum et al. | 526/312 |
| 4,070,246 | 1/1978 | Kennedy et al. | 252/62.54 |

*Primary Examiner*—George F. Lesmes
*Assistant Examiner*—E. Rollins Buffalow
*Attorney, Agent, or Firm*—Marvin E. Jacobs

[57] ABSTRACT

Suspension polymerization of aqueous glutaraldehyde in basic conditions in presence of surfactants such as isobutoxy acrylamide copolymers and/or cross-linking agents yield cross-linked, water insoluble glutaraldehyde polymer microspheres ranging in size from 200 Å to 10μ. Addition of fluorochromes, e.g., FITC, during polymerization yields microspheres of high fluorescent intensity and addition of a suspension of metal containing particles such as $Fe_3O_4$ during polymerization yields magnetic microspheres. Immunopolyglutaraldehyde microspheres can be obtained by interacting the polyglutaraldehyde microspheres with antibodies. The immunomicrospheres were used to label and separate cell subpopulations. The labeling specificity is considerably improved by increasing the amount of isobutoxy polyacrylamide incorporated in the microspheres.

15 Claims, No Drawings

POLYGLUTARALDEHYDE MICROSPHERES

ORIGIN OF THE INVENTION

The invention described herein was made in the course of work under a grant from the Department of Health, Education and Welfare.

BACKGROUND OF THE INVENTION

1. Field of the Invention

The present invention relates to the synthesis of polyglutaraldehyde microspheres, fluorescent and magnetic variations thereof, protein conjugates thereof and to the use of the conjugates in biological and chemical research and testing.

2. Description of the Prior Art

The isolation and characterization of cell membranes and their components is essential for an understanding of the role in which surface membranes play in regulating a wide variety of biological and immunological activities. The present techniques used for this purpose are not quite satisfactory.

Knowledge of the nature, number and distribution of specific receptors on cell surfaces is of central importance for an understanding of the molecular basis underlying such biological phenomena as cell-cell recognition in development, cell communication and regulation by hormones and chemical transmitters, and differences in normal and tumor cell surfaces. In previous studies, the localization of antigens and carbohydrate residues on the surface of cells, notably red blood cells and lymphocytes, has been determined by bonding antibodies or lectins to such molecules as ferritin, hemocyanin or peroxidase which have served as markers for transmission electron microscopy. With advances in high resolution scanning electron microscopy (SEM), however, the topographical distribution of molecular receptors on the surfaces of cell and tissue specimens can be readily determined by similar histochemical techniques using newly developed markers resolvable by SEM.

Recently, commercially available polystyrene latex particles have been utilized as immunologic markers for use in the SEM technique. The surface of such polystyrene particles is hydrophobic and hence certain types of macromolecules such as antibodies are absorbed on the surface under carefully controlled conditions. However, such particles stick non-specifically to many surfaces and molecules and this seriously limits their broad application.

The preparation of small, stable spherical Poly-Hema particles which are biocompatible, i.e., do not interact non-specifically with cells or other biological components and which contain functional groups to which specific proteins and other biochemical molecules can be covalently bonded is disclosed in U.S. Pat. No. 3,957,741.

Smaller, more evenly shaped acrylic microspheres are disclosed in U.S. Pat. No. 4,138,383. Microspheres having a density differing from that of cell membranes are disclosed in U.S. Pat. No. 4,035,316 and fluorescent-acrylic copolymer microspheres are disclosed in Ser. No. 718,104 filed Aug. 27, 1976.

The hydroxyl groups can be activated by cyanogen bromide for covalent bonding of proteins and other chemicals containing amino groups to the polymeric bead. Methacrylic acid residues which impart a negative charge onto the particles are likely to prevent non-specific binding to cell surfaces and to provide carboxyl groups to which a variety of biochemical molecules can be covalently bonded using the carbodiimide method.

The derivatization procedure is unnecessarily complex and requires an additional step to prepare the bead surface for covalently binding to proteins such as antibodies, lectins and the like or other molecules such as DNA, hormones and the like. Therefore, the method of derivatization of acrylic microbeads is tedious and availability is limited. Monomeric glutaraldehyde has been used as a biochemical reagent to covalently bond proteins such as immunoglobulins to ferritin polymeric microspheres and other small particles which were then utilized to map receptors on cell membranes. However, the reaction mechanism of proteins with glutaraldehyde is difficult to ascertain since its structure is still not clear and it has been reported to be in equilibrium with cyclic and hydrated forms. The reaction is difficult to carry out and frequently gives unsatisfactory results.

Direct protein bonding polyglutaraldehyde is disclosed in copending application Ser. No. 021,989, filed concurrently herewith prepared by solution polymerization in aqueous basic medium. In contrast to monomeric glutaraldehyde, the polymer contains conjugated aldehyde groups. This imparts stability to the Schiff's bases formed after reaction with proteins and, further, since the hydrophilic polyglutaraldehyde has relatively long chains extending from the surface into the surrounding aqueous medium, the heterogenous reaction with protein is facilitated.

Soluble polyglutaraldehyde (PGL) can be used for casting into film or for coating surfaces of substances such as polymeric microbeads, particularly amine or hydrazide substituted beads. Polyglutaraldehyde can be converted to a fluorescent polymer by reaction with non-fluorescent reagents such as m-aminophenol. Polyglutaraldehyde microspheres can be directly prepared by suspension polymerization with stirring in presence of surfactant or by precipitation from solution containing surfactant. Magnetic, high density or electron dense microspheres can be prepared by coating metal particles or by suspension polymerization of glutaraldehyde in presence of a suspension of finely divided metal or metal oxide.

It has been determined that the PGL microspheres exhibit some degree of non-specific binding to cells. Moreover, though some cross-linking occurs during the homopolymerization of glutaraldehyde, the polymer can be dissolved in highly polar solvents.

SUMMARY OF THE INVENTION

It has now been discovered in accordance with the invention that the copolymerization of 0.1% to 10%, preferably 1 to 5%, of cross-linking agent with glutaraldehyde results in microspheres insoluble even in polar solvents. When polyamides such as isobutoxypolyacrylamide are incorporated into the microsphere, the latter do not exhibit non-specific binding to cell membranes. In a preferred mode of polymerization, the amide groups are provided by the surfactant and are at least partially incorporated into the microspheres.

These and many other advantages and attendant features of the invention will become apparent as the invention becomes better understood by reference to the following detailed description.

DESCRIPTION OF THE PREFERRED EMBODIMENTS

PGL microspheres are prepared from aqueous solution containing 1% to 50% by weight of monomeric glutaraldehyde and 0.1 to 10% of surfactant or cross-linking agent by raising the pH of the solution above 7, preferably from 9 to 12. The reaction occurs at room temperature.

Analysis by UV or IR spectroscopy confirms the presence of conjugated aldehyde functional groups in the PGL microsphere which form stable bonds with amino-containing molecules such as proteins.

The PGL microspheres exhibit a small amount of fluorescence. However, reaction with specific reagents that are not in themselves fluorescent, results in a fluorescent microsphere by forming fluorescent chromophores attached to the polymer. Anthrone reacts with acrolein units to form a benzanthrone fluorogen and m-aminophenol reacts with the acrolein structure to form the fluorogen, 7-hydroxyquinoline. Aminofluorescein also reacts with aldehyde groups to form fluorescent microspheres.

The microspheres are preferably very small in size from 200 Å to 100 microns, generally from 500 Å to 10 microns so that specific receptor sites on a cell surface can be tagged.

Suspension polymerization of glutaraldehyde and cross-linking agent in presence of an emulsifying agent yields water-insoluble, polyglutaraldehyde (PGL) microspheres having a diameter from 200 Å to 10μ, usually from 500 Å to 1.5μ. Polymerization in presence of a suspension of magnetic particles results in the formation of magnetic microspheres. Fluorescent microspheres can be formed by post-polymerization reaction with a fluorochrome or by polymerization in the presence of a fluorochrome.

The size of microspheres is affected by pH, concentration of surfactant and concentration of glutaraldehyde monomer. The microspheres are prepared by forming a suspension of 0.1% to 20% by weight glutaraldehyde, 0.1 to 10% cross-linking agent, 0.1 to 3% surfactant in aqueous media, adjusting the pH from 7 to 13, preferably 9–11.5 and stirring for several hours. PGL microspheres, are then separated and washed. The aqueous media may contain 5% to 50% by weight of immiscible organic liquids such as aromatic or aliphatic organic solvents, suitably benzene, toluene, hexane, heptane, octane or triglycerides such as cotton seed oil, corn oil or soybean oil.

Small microspheres (of the order of 100 to 500 Å) containing electron-dense metals provide higher spatial resolution of cell surface features. Immunomicrospheres containing electron-dense metals provide more stable labels than gold particles with physically absorbed antibodies that are presently used for cell labeling. The metal containing microspheres can be synthesized by, in situ, polymerization of the microspheres in presence of a suspension of finely-divided metal particles or compounds of the metal, preferably a colloidal dispersion of the metal. The metal is incorporated into the microsphere in an effective amount of from 0.5% to 40% by weight, generally from 5% to 25% by weight.

The metal or metal compound particles are preferably fine, evenly sized materials having a uniform diameter smaller than the resultant microsphere diameter, typically below 1000 Å, generally from 25 Å to 500 Å. The metals are preferably the electron-dense heavy metals having a high atomic number above 50, preferably above 75 such as Pb, Ni, Co, Pt, Au, Fe. The metal may be magnetically attractable such as Fe, Ni, Co or alloys thereof or an inorganic magnetic compound such as a metal oxide. The magnetic material is preferably a magnetic iron oxide of the formula $Fe_3O_4$. Some hard, ceramic type ferrites, such as lithium ferrites can also be used. The metal or compound can be made into a readily dispersible form by suspension in water containing a surfactant such as polyethylene imine.

The microspheres can be rendered fluorescent by reaction with anthrone or m-aminophenol or with dyes containing aldehyde or hydroxyl reactive groups such as aminofluorescein, 9-amino acridine, propidium bromide or fluorescein isothiocyanate (FITC). Highly fluorescent microspheres can also be prepared by suspension polymerization of glutaraldehyde in presence of fluorochromes containing groups capable of reaction with aldehyde or hydroxyl.

The surfactants are water soluble, nonionic, cationic or anionic materials, generally organic which is defined to include fluorocarbon and hydrofluorocarbon and silicon compounds. Cationic surfactants can be amines, amine salts, sulfonium, phosphonium or quarternary ammonium compounds. The surfactants may be utilized alone or in presence of 1 to 5% by weight of a suspending agent such as a polyethylene oxide, glycerine, polyacrylamide or a polyethylene imine. Representative cationic surfactants are Zonyl FSC (Dupont) which is a cationic substituted fluorocarbon and Guar C13 (Stein and Hall Specialty Chem.) which is a cationic guar gum. Water-soluble, anionic surfactants can be selected from the commercially available carboxylic acids, sulfuric esters and alkane sulfonic acids, for example, Zonyl FSP (Dupont) which is an anionic substituted fluorocarbon.

Nonionic surfactants are usually the polyethylene oxide and/or polypropylene oxide derivatives of phenol, alcohols or fatty acids. Preferred non-ionic surfactants are water-soluble copolymers having molecular weights from 880 to 10,000 of acrylamide with 30–60% by weight of acrylic esters or alkyl- or alkoxy-alkyl acrylamides such as isobutoxymethacrylamide as disclosed in U.S. Pat. No. 4,098,987.

Glutaraldehyde polymerizes to form repeating units of the structure:

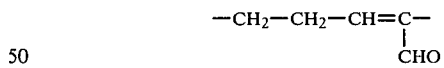

The cross-linking agents are water-soluble or dispersible organic compounds containing at least two functional groups reactive with the conjugated aldehyde groups such as amine, hydroxyl, imine, mercaptan and, amide. Representative classes of cross-linking agents are low molecular weight compounds containing 2-20 carbon atoms, for example, diamines or triamines such as ethylene diamine, melamine, cyanuric chloride or 1,6-diamino hexane; diols or triols such glycerine, pentaerythritol or ethylene glycol; or poly- or di-thiomercaptans such as glycol dithiomercaptoacetate pentaerythritol tetrathioglycolate.

Copolymerization in presence of the low molecular cross-linking agents may require higher polymerization temperatures such as 20° C. to 50° C. or higher. Polymeric cross-linking agents may be selected from polyethylene imine, polyethylene glycols, or acrylamide polymers such as polyacrylamide, polymethylolacrylamide and preferably the surface active copolymers of acrylamide and alkyl or alkyloxy-alkyl acrylamides such as isobutoxymethacrylamide.

EXAMPLE 1

Commercial glutaraldehyde was purified by means of activated carbon. An aqueous solution of 25% glutaraldehyde and 0.5%, 1,6-diaminohexane was polymerized at 25° C. by adjusting the pH to 11.5 with NaOH. After two hours, the temperature was raised to 50° C. and the mixture stirred for 8 hours. The copolymer was precipitated, filtered, washed with water and dried (Yield 65%).

When 5% aqueous glutaraldehyde and 0.05% ethylene diamine were polymerized with stirring at 25° C. and at pH 11 in presence of 3% Triton X-100, microspheres having a diameter of about 1 micron were recovered.

EXAMPLE 2

To a 5% (w/v) aqueous glutaraldehyde solution (100 cc) containing 1% (w/v) of Aerosol 604 surfactant (American Cyanamid) Co.—copolymer of 60% acrylamide—40% isobutoxymethacrylamide), 10 N NaOH was added dropwise until a pH of 11 was reached. The mixture was then deaerated with nitrogen, the container tightly closed and placed on a mechanical shaker for 24 hours at room temperature. After 1, 2 and 4 hours of reaction time the pH was adjusted to 11 by addition of 10 N NaOH. The mixture was subsequently extensively dialyzed against water and then centrifuged three times at 2000 G (30 min.). The PGL spheres (Yield: 200 mg) of an average diameter of 2000 Å as determined by scanning electron microscopy, could be redispersed in 0.01 M, (pH 7.4) phosphate buffer saline (PBS) or distilled water. By varying the concentration of surfactant, monomer of pH the size of microspheres could be altered in a predictable way.

Fourier Transform Infra Red (FTIR) absorption spectra indicate that in addition to the absorption bands assignable to non-conjugated aldehyde groups, conjugated aldehyde groups and carbon-carbon double bonds (1720, 1680 and 1635 cm$^{-1}$) an additional absorption at 1540 cm$^{-1}$ is due to a component of the copolymerized acrylamide-isobutoxy methacrylamide surfactant.

EXAMPLE 3

Example 2 was repeated in the presence of 1% w/v Ferrofluid (aqueous dispersion of $Fe_3O_4$ containing 5% w/v iron) resulted in the formation of magnetic microspheres having an average diameter of $0.1+0.02\mu$. The purification of iron containing microspheres consisted of dialysis against water and separation from diamagnetic impurities by means of a permanent magnet. The material was finally dispersed in phosphate buffered sucrose (0.25 M) or water.

EXAMPLE 4

Dispersible iron oxide was prepared by dissolving 10 g of ferrous chloride and 13.5 g of ferric chloride in 210 cc of 1% w/v polyethylene imine (M.W. 1800) aqueous solution. 50% NaOH was added to pH 7. The reaction mixture was refluxed for 3 hours, dialyzed extensively against water and separated magnetically three times from non-magnetic particles. The magnetic polyethylene imine-iron oxide particles were redispersed in water and then sonicated with a clinical sonicator for 10 minutes. Magnetic particles having a diameter of 300 Å with amine groups on the surface were formed.

EXAMPLE 5

1% polyethylene imine-iron oxide from Example 4 was added to the suspension polymerization system of Example 2 and resulted in the formation of magnetic microspheres.

EXAMPLE 6

The addition of 0.01% FITC solution in ethylene diamine to the suspension polymerization system of Example 2 resulted in magnetic fluorescent microspheres having an average diameter of $0.1\mu$.

EXAMPLE 7

20 mg of the magnetic microspheres from Example 3 were shaken at 25° C. for 24 hours with 1 mg of FITC dissolved in 0.02 cc of distilled ethylene diamine. The highly fluorescent, magnetic, PGL microspheres were dialyzed extensively against water and then separated 3 times magnetically. The purified microspheres were redispersed in water or phosphate buffered sucrose (0.25 M).

EXAMPLE 8

Non-magnetic and magnetic microspheres were produced according to the procedures of Examples 2 and 3 except that the amount of Aerosol 604 was varied from 1% to 20% w/v. Nitrogen analysis of the microspheres is presented in the following table:

TABLE 1

| Aerosol 604, % w/v | Magnetic, % N | Non-Magnetic, % N |
|---|---|---|
| 1 | 1.52 | 2.19 |
| 2 | — | 3.79 |
| 5 | 3.61 | — |
| 7 | — | 5.57 |
| 20 | 5.68 | 8.05 |

The copolymerization of the isobutoxyacrylamide surfactant is confirmed by nitrogen analysis, the amount of nitrogen increasing with increased amounts of the Aerosol 604. The IR peak at 1540 cm$^{-1}$ also increases with increasing amounts of Aerosol 604.

Cross-linking was confirmed by dissolving PGL homopolymer and Aerosol 604 - glutaraldehyde copolymers in DMSO. The solubility data follows.

| % Aerosol 604 | % Polymer Dissolved |
|---|---|
| 0 | 80 |
| 1.25 | 55 |
| 10.1 | 23 |

The increasing insolubility of the copolymers demonstrates the cross-linking effect of the comonomer.

Labeled cells and magnetic separation

The marking of cell surface receptors by means of fluorescent, non-fluorescent or magnetic fluorescent PGL microspheres was found to be simple and efficient as evidenced by numerous tests using fixed human or turkey rbc as models. Preliminary experiments with live human lymphocytes to label IgG molecules on B cells were also successful.

EXAMPLE 10

Labeling of human rbc

An aqueous PGL microsphere suspension (0.3 cc, 2 mg of spheres/cc, diameter 2000 A) was added to a PBS solution of purified goat antirabbit (0.2 mg containing 0.2 cc of PBS). The mixture was gently agitated for 3 hours at 4° C. Glycine was then added (10 mg) and the agitation was continued for another hour. Unbound antibody was separated by passing the suspension through a sepharose 4B column (1.5×20 cm). The separation was monitored spectrophotometrically at $\lambda = 280$ nm (Cary 14).

Human rbc from a normal donor and fixed with glutaraldehyde were sensitized with rabbit antihuman rbc. The rbc ($10^7$) suspended in 0.5 cc of PBS containing the antiserum (0.2 mg) were agitated for 30 min at room temperature and the cells were separated and washed three times by spinning the PBS suspension in an international centrifuge at 500 G. The goat antirabbit derivatized microspheres were then added to the pellet of sensitized human rbc and the mixture was gently agitated for 1 hour at 4° C. The rbc were then separated from unreacted conjugated microspheres by centrifugation (3 times at 500 G). The labeled cells were resuspended in PBS (0.4 cc) and examined in the light or scanning electron microscope (SEM).

Two controls were used in each experiment: (1) microspheres were conjugated with human IgG and interacted with sensitized rbc; and (2) microspheres conjugated with goat antirabbit IgG interacted with non-sensitized rbc.

Labeling of human lymphocytes

The labeling of live human lymphocytes by means of PGL microspheres was tested.

PGL microspheres (2000 Å in diameter) were conjugated with FITC tagged human IgG as described in Example 10. The number of labeled Fc receptors was counted under the fluorescent microscope and agreed with values obtained in the literature within ±10%.

The separation of magnetically labeled human rbc was achieved in the following way:

Mixtures of human rbc with the following ratios of unlabeled to labeled cells were prepared: 1:1, 7:1 and 9:1. The mixtures (10 cc) were gently stirred in a glass vial fitted with a horseshoe magnet (300 gauss). At the end of two hours, cells which were not attracted to the vessel walls were isolated. Cells attracted by the magnet were diluted with 10 cc of PBS and the magnetic separation was repeated. SEM examination showed that 95% of unlabeled cells could be thus separated from all three synthetic mixtures.

The extent of non-specific interaction with live human lymphocytes as well as the efficiency of magnetic separation of cell subpopulations by means of magnetic sorter is at present under investigation.

A new convenient immunoreagent in form of PGL microspheres was synthesized in a variety of sizes and with a relatively narrow size distribution. High intensity of fluorescence can be imparted to the PGL microspheres during the synthesis which still leaves a high concentration of aldehyde groups on the surface. The aldehyde functional groups permit covalent bonding with antibodies, enzymes and other proteins in a single step. Therefore this immunoreagent eliminates the previously used intermediate steps in which the cyanogen bromide and carbodiimide reaction was used. The wide range of ionic strength and pH without occurrence of aggregation and the high specificity of the PGL microspheres, at least as far as human rbc is concerned, are also desirable properties.

A minor synthetic modification yields fluorescent magnetic PGL microspheres for a large number of potential applications.

The use of magnetic particles has created a great deal of interest in biochemical research and clinical medicine when used as supports for immobilized enzymes. Their easy retrieval from liquors containing colloids and undissolved solids should be of practical value. The separation of proteins and chemical compounds by affinity chromatography can be simplified by elimination of tedious centrifugation procedures and column chromatography steps. Magnetic particles have also recently been tested in radioimmunoassay techniques in hyperthermia treatment of cancer, in guidance of magnetic particles to a vascular malformation such as cerebral aneurism with the intent to seal the defect by inducing thrombosis.

Other proposed applications have been as tracers of blood flow or vehicles for drug delivery. The first successful application of magnetic immunomicrospheres to the separation of B and T cells has been demonstrated. These results were later confirmed using C-1300 neuroblastoma cells. There is little doubt that physical sorting of cell sub-populations has become a necessity. Many separation methods, while useful are limited by the restricted set of parameters upon which separation can be based and by the fact that they are batch techniques.

New flow cytometers and sorters permit quantitative multiparameter measurements and sorting based on these measurements, but are limited as far as the number of cells that can be separated in a given time. Magnetic cell sorters have the potential of cell separation in a continuous process. The evidence obtained in the present investigations using model cell systems indicates that magnetic PGL immunomicrospheres of desirable sizes can be conjugated with proteins in a simple and convenient manner, therefore offer a potential for large scale immunological cell sorting as well as other applications.

EXAMPLE 11

3.3 cc of the polyethylene imine-iron oxide suspension from Example 4 (29 mg/cc of magnetic particles) were combined with 0.1 cc of 50% monomeric glutaraldehyde and 0.22 cc of Aerosol 604 and water added to form 10 cc of suspension at pH 7. The suspension was stirred on a shaker for 24 hours and dialyzed and magnetically purified. A stable suspension of magnetic particles about 500 Å in diameter containing aldehyde groups on the surface was recovered.

It is to be understood that only preferred embodiments of the invention have been described and that numerous substitutions, modifications and alterations are permissible without departing from the spirit and scope of the invention as defined in the following claims.

What is claimed is:

1. Microspheres having a diameter from 200 Å to $10\mu$ consisting essentially of water-insoluable copolymer of glutaraldehyde having a repeating conjugated aldehyde containing unit of the formula:

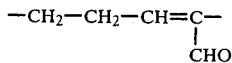

cross linked with 0.1 to 10% by weight of a water-dispersible or water-soluble organic cross-linking agent containing at least two functional groups reactive with said aldehyde group selected from amine, hydroxyl, imine mercaptan or amide and said microspheres containing 0.5 to 40% by weight of metal containing particles having an atomic number above 50 and a diameter below 1000 Å.

2. Microspheres according to claim 1 in which the cross-linking agent is also a surfactant.

3. Microspheres according to claim 2 in which the cross-linking agent is an acrylamide polymer.

4. Microspheres according to claim 3 in which the cross-linking agent is a copolymer of 10 to 70% acrylamide and 10 to 70% of an alkyl-acrylamide or an alkyloxyalkyl acrylamide.

5. Microspheres according to claim 1 in which the cross-linking agent contains 2 to 20 carbon atoms.

6. Microspheres according to claim 5 in which the cross-linking agent is a diamine.

7. Microspheres according to claim 1 in which the particles are magnetically attractable.

8. Microspheres according to claim 7 in which the particles comprise $Fe_3O_4$.

9. Microspheres according to claim 1 containing fluorogen groups.

10. Microspheres according to claim 9 in which the fluorogen groups are the reaction products for acrolein groups and a compound that forms a fluorogen on reaction with said groups.

11. Microspheres according to claim 9 in which the fluorogen is the reaction product of aldehyde groups with an aldehyde reactive fluorochrome.

12. Microspheres according to claim 11 in which the fluorochrome is selected from aminofluorescein, 9-amino acridine, propidium bromide, or fluorescein isothiocyanate.

13. Microspheres according to claim 1 bound to protein through said aldehyde groups.

14. Microspheres according to claim 13 in which the protein is selected from antibodies, antigens, immunoglobulins, lymphocytes or hemoglobin.

15. Microspheres according to claim 14 in which the protein is an antibody.

* * * * *